(12) United States Patent
Chételat et al.

(10) Patent No.: US 12,251,149 B2
(45) Date of Patent: Mar. 18, 2025

(54) REMOTELY POWERED COOPERATIVE SENSOR DEVICE

(71) Applicant: CSEM Centre Suisse d'Electronique et de Microtechnique SA—Recherche et Développement, Neuchâtel (CH)

(72) Inventors: Olivier Chételat, Cudrefin (CH); Benjamin Bonnal, Neuchâtel (CH); André Fivaz, Les Ponts-de-Martel (CH)

(73) Assignee: CSEM Centre Suisse d'Electronique et de Microtechnique SA—Recherche et Développement, Neuchâtel (CH)

( * ) Notice: Subject to any disclaimer, the term of this patent is extended or adjusted under 35 U.S.C. 154(b) by 461 days.

(21) Appl. No.: 17/111,687

(22) Filed: Dec. 4, 2020

(65) Prior Publication Data

US 2021/0169543 A1 Jun. 10, 2021

(30) Foreign Application Priority Data

Dec. 5, 2019 (EP) ..................................... 19213839

(51) Int. Cl.
*A61B 5/053* (2021.01)
*A61B 5/00* (2006.01)
(Continued)

(52) U.S. Cl.
CPC .............. *A61B 18/00* (2013.01); *A61B 5/053* (2013.01); *A61B 5/308* (2021.01); *A61B 5/7228* (2013.01);
(Continued)

(58) Field of Classification Search
None
See application file for complete search history.

(56) References Cited

U.S. PATENT DOCUMENTS

| 2011/0251817 A1* | 10/2011 | Burns | A61B 5/7203 |
| | | | 702/104 |
| 2015/0173677 A1 | 6/2015 | Chetelat et al. | |
| 2016/0058315 A1* | 3/2016 | Wiser | A61B 5/6821 |
| | | | 600/479 |

FOREIGN PATENT DOCUMENTS

| EP | 2567657 A1 | 3/2013 |
| WO | 0154563 A2 | 8/2001 |

OTHER PUBLICATIONS

Search Report issued in European Patent Application No. 19213839 dated Jun. 2, 2020.

(Continued)

*Primary Examiner* — Aurelie H Tu

(74) *Attorney, Agent, or Firm* — McDonald Hopkins LLC

(57) ABSTRACT

A sensor for potential and/or impedance measurements on a body including at least one sensor connected to a master; the master including a power supply supplying a power signal transmitted to the at least one sensor; said at least one sensor including a first sensor fork sub-circuit configured to supply a positive current to a first circuit branch and a negative current to a second circuit branch; the at least one sensor further including a control circuit configured for controlling the positive and/or negative current in order to transmit an information signal to the master, and/or to control a first controlled signal to a first desired signal; and a second electrical connection connecting the at least one sensor to the master; the control circuit being further configured for harvesting energy from the alternating voltage supplied by the master to power the at least one sensor.

4 Claims, 7 Drawing Sheets

(51) Int. Cl.
  *A61B 5/308* (2021.01)
  *A61B 18/00* (2006.01)
(52) U.S. Cl.
  CPC ............. *A61B 2018/00702* (2013.01); *A61B 2018/00833* (2013.01); *A61B 2018/00839* (2013.01); *A61B 2018/00845* (2013.01); *A61B 2018/00875* (2013.01); *A61B 2560/0214* (2013.01)

(56) References Cited

OTHER PUBLICATIONS

Michael Rapin et al: "Cooperative sensors: a new wired body-sensor network approach for wearable biopotential measurement", Proceedings of the 5th EAI International Conference on Wireless Mobile Communication and Healthcare, "Transforming Healthcare Through Innovations in Mobile and Wireless Technologies", Oct. 14-16, 2015, Mobihealth, London, Great Britain, XP055693487.
Archive of Wikipedia page on Current Mirror, https://web.archive.org/web/20190908050725/https:/en.wikipedia.org/wiki/Current_mirror; last edited Aug. 21, 2019.
Archive of Wikipedia page on Differential Amplifier, https://web.archive.org/web/20190224133031/https:/en.wikipedia.org/wiki/Differential_amplifier; last edited Dec. 21, 2018.

\* cited by examiner

REMOTELY POWERED COOPERATIVE SENSOR DEVICE

FIELD

The present invention relates to the field of electronic circuits for potential and/or impedance measurements, in particular in the context of medical wearables.

DESCRIPTION OF RELATED ART

Cooperative sensors with communication were first introduced in European patent EP2567657 from the present applicant. Cooperative sensors include a master (or reference unit) using a voltage source to broadcast (transmit) synchronization and control information to sensors. The master coordinates the functioning of the sensors, such as sampling and current injection when performing measurements, and the sensors send information related to measurements to the master via current sources comprised in the sensors. The cooperative sensor can measure a potential and an impedance using active electrodes, which allows immunity with respect to ambient electric field variations, even without shielded cables.

Cooperative sensors are typically powered by having their own floating power supply, usually a rechargeable battery. Having a power supply on the sensor allows for measuring a plurality of signals, since most sensors require amplification or driving electronics. It further allows using actuators (e.g., buzzer, ultrasound or acoustic emitters, electrical stimulation, heating, etc.). Moreover, cooperative sensors inherit the features of active electrodes but can be connected to a bus (i.e., in parallel) instead of being connected in a star arrangement as would be the case with active electrodes. Depending on the connection topology, the bus can comprise one, two or more wires.

Providing the cooperative sensors with a central power supply would be advantageous but is difficult to achieve. Indeed, using the wires already used for sensing functions (measurements, synchronization and bi-directional communication between the cooperative sensors and the master) to power the sensors risks interfering the sensing functions. Increasing the number of wires in the bus may decrease reliability and increase manufacturing cost.

Moreover, in the context of medical devices, the allowed auxiliary current is limited to 10 µA by the standard IEC 60601-1 (in normal condition and class CF) and when measured with a low-pass filter at 1 kHz and a 1 kΩ resistance). Since the bus is an applied part (the expressions in italic are used in accordance with the IEC 60601-1 definition), adding two additional (uninsulated) wires to the bus in order to supply power to the sensors limits the voltage considered as safe to 10 mV. However, a voltage suitable for powering should rather be about 3 V requiring insulation of the wires. In the context of wearables, where tear and wear and the presence of body fluid are to be expected, having reliable insulation is not easily achieved, especially when the sensors are to be connected in a way that is seamless, flexible, stretchable, breathable, and washable. Cost can also be an issue, as well as manufacturability and reliability.

Document US2015173677 discloses a measurement device for measuring a bio-impedance and/or a bio-potential of a human or animal body. The measurement device includes at least two electrode sensors and is adapted to be worn on the body. Each electrode sensor includes a first electrical contact configured to be in electrical contact with the skin of the body when the system is worn, and a second electrical contact. A single electrical connector electrically connects the at least two electrode sensors with each other via the second electrical contact. Each electrode sensor comprises a power supply.

Despite the above drawbacks, it remains highly desirable to obtain a cooperative sensor solution comprising a central battery.

SUMMARY

The present disclosure concerns a sensor for potential and/or impedance measurements on a body, comprising at least one remotely powered sensor connected to a master; the master comprising a receiver and a power supply configured to supply an alternating power voltage to said at least one sensor, the alternating power voltage corresponding to a synchronization and/or communication signal; said at least one sensor comprising a control circuit including a first sensor fork sub-circuit configured to supply a positive current to a first circuit branch and a negative current to a second circuit branch; the control circuit further comprising a control sub-circuit configured for controlling the positive and/or negative current in order to transmit an information signal to the receiver, and/or to control a first controlled signal to a first desired signal; the sensor further comprising a first electrical connection and a second electrical connection connecting said at least one sensor to the master. The power supply is configured to supply the alternating power voltage at a powering frequency band. The control circuit is further configured for harvesting energy from the power alternating voltage to power said at least one sensor and for controlling the positive or negative current at a control frequency band corresponding to a range of frequencies used for potential and impedance measurements or for communication and not overlapping the frequencies of the powering frequency band.

The sensor described herein is particularly advantageous for potential and impedance measurements, e.g., in humans, animals, plants, soil, rocks, etc. Here, potential measurements may include measurement of bio-potentials in humans, for instance ECG (electrocardiogram), EEG (electroencephalogram), or EMG (electromyogram). Impedance measurements may include bio-impedance, such as transthoracic impedance for respiration monitoring, bio-impedance spectroscopy (BIS) for body composition analysis, EIT (electrical-impedance tomography), skin impedance, or EDA (electro-dermal activity, also called galvanic skin response).

The sensor is particularly suitable for dry-electrode measurements. The sensor requires only one or two electrical connections. Since the sensors are connected to a same bus, a large number of sensors can be used. The sensor can be used for capturing a plurality of functional images. The cooperative sensor device is also suitable for high integration of sensor arrays, such as implantable electrode arrays where, for example, each electrode can take the form of a die mounted on a flexible substrate. The one or two electrical connections is also advantageous when the sensor is used in combination with wearables, where safety is important, especially despite insulation failure due to tear and wear or to the presence of body fluid. Since the sensor can comprise amplifiers or current sources having very high impedance, it can be used in several other application fields, such as potentiometric sensor.

The power voltage can be an alternating voltage. The power voltage can be alternating in a powering frequency band not overlapping the potential (ECG) and/or impedance (EIT) measurements.

The control circuit can comprise an adder providing a difference signal corresponding to the sum of the first desired signal and the opposite of the first controlled signal; the difference signal being inputted in the controller in order to control the first controlled signal by a first component of a transfer function of the controller.

The first and second electrical connections can comprise an electrically conductive element.

The fork sub-circuit can comprise two diodes. Moreover, the control circuit can comprise a block LOGIC powered from capacitances; the block LOGIC being inputted by a clock signal taken at a node between the two diodes and being configured for dividing the clock signal.

The control circuit can comprise an operational amplifier setting the positive and negative currents.

BRIEF DESCRIPTION OF THE DRAWINGS

The invention will be better understood with the aid of the description of an embodiment given by way of examples and illustrated by the figures, in which:

FIGS. 3a to 3g illustrate variant examples of implementation of a control sub-circuit comprised in the cooperative sensor device;

DETAILED DESCRIPTION OF POSSIBLE EMBODIMENTS

Figure 1:
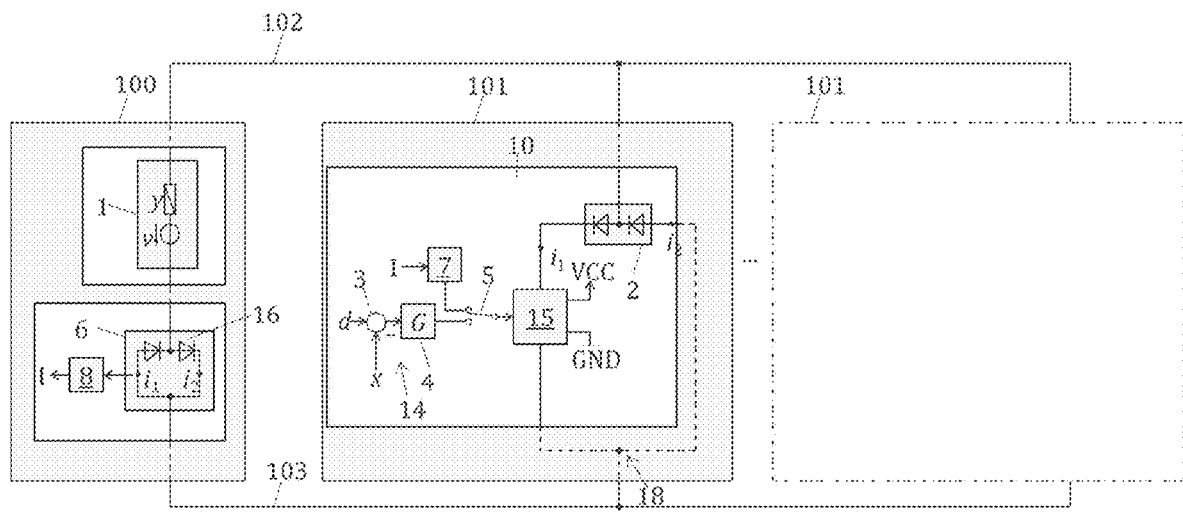
FIG. 1 illustrates schematically a cooperative sensor device for potential and/or impedance measurements, according to an embodiment.

FIG. 1 illustrates schematically a cooperative sensor device for potential and/or impedance measurements on a body (not shown in FIG. 1), comprising at least one sensor 101 connected to a master 100. The master 100 comprises a receiver 6 and a power supply 1 supplying a power voltage v to said at least one sensor 101. The sensor 101 comprises a control circuit 10 including a first sensor fork sub-circuit 2 configured to supply a positive current $i_1$ to a first circuit branch and a negative current $-i_2$ to a second circuit branch. The control circuit 10 further comprises a control sub-circuit 15 configured for controlling the positive and/or negative current $i_1$, $-i_2$ in order to transmit an information signal I to the receiver 6, and/or to control a first control signal x to a first desired signal d. The device further comprises a first electrical connection 102 and a second electrical connection 103 connecting said at least one sensor 101 to the master 1. The control circuit 10 is further configured for harvesting energy from the power voltage v to power the sensor 101 (or the several sensors 101).

In the configuration of FIG. 1, a first electrical connection 102 connects the power supply 1 to the first sensor fork sub-circuit 2 and a second electrical connection 103 connects the receiver 6 to the control circuit 10 (and possibly to the first sensor fork sub-circuit 2).

Although only one sensor 101 is represented in FIG. 1, the cooperative sensor device can comprise a plurality of sensors 101 connected to the master 100 via the electrical connections 102, 103.

The cooperative sensor device is destined to be placed in contact with a body (see FIG. 2) when performing the potential and/or impedance measurements. Here, the term "body" can be used to describe a body or surface of humans, animals, plants, soil, rocks, etc., on which the potential and impedance measurements are performed.

The power voltage v supplied by the master 100 to the sensor 101 can correspond to a synchronization/communication signal.

In FIG. 1, the power supply 1 is represented as an alternating voltage source modelled by its Thevenin equivalent, i.e., a voltage source v and a series impedance y. The voltage source v can provide a power voltage v alternating at a powering frequency band. Here, the powering frequency band can correspond to a frequency not overlapping the frequencies of the potential and impedance measurements (see below), thereby limiting the disturbance the power voltage v can make on the tiny measurement signal. Having the frequency of the power voltage v in a different frequency band than the one of the measurement signal further allows the acquisition chain to include filters to reduce the disturbance (for instance a filter with a zero at the powering frequency). For instance, the power voltage v can be a 1 MHz square wave of ±1.65 V (e.g., digital clock with 3.3 V logic).

The alternating power voltage v has also the advantage that its signal edges can be used by the sensor 101 as synchronization information, so that the master 100 and sensor 101 work in concert according to the alternating power voltage v. For example, a 1 MHz square wave voltage v can provide a 1 MHz clock and if the voltage v includes some exceptions (for example a clock signal at a different frequency), for instance if every 1 s a period of 1 μs is slowed down to 2 μs, the sensors 101 can detect them to be synchronized at 1 Hz.

More complex pattern of the power signal may allow broadcasting (transmitting) additional information to all sensors 101, for instance for configuration or control of the sensors. Another advantage to use high frequency alternating power voltage v is that the standard IEC 60601-1 includes a 1 kHz low-pass filter in its definition of allowed auxiliary currents. This means that if 10 μA represents the maximum allowed current at low frequencies, at 10 kHz, this maximum can be increased up to 100 μA and up to 10 mA at 1 MHz. The standard IEC 60601-1, however, specifies an absolute limit to 10 mA. It is therefore not useful to use frequencies higher than 1 MHz. A simple way to fulfil the safety requirements could therefore to have a power supply 1 with current limited to 10 mA and working at 1 MHz. This would even allow the powering of the sensors 101 with only the first electrical connection 102 being an electrically conductive element that is not the body 104, such as an electrically conductive trace, wire, etc., wherein the return second electrical connection 103 being the body 104 itself (see FIG. 2).

Figure 4:
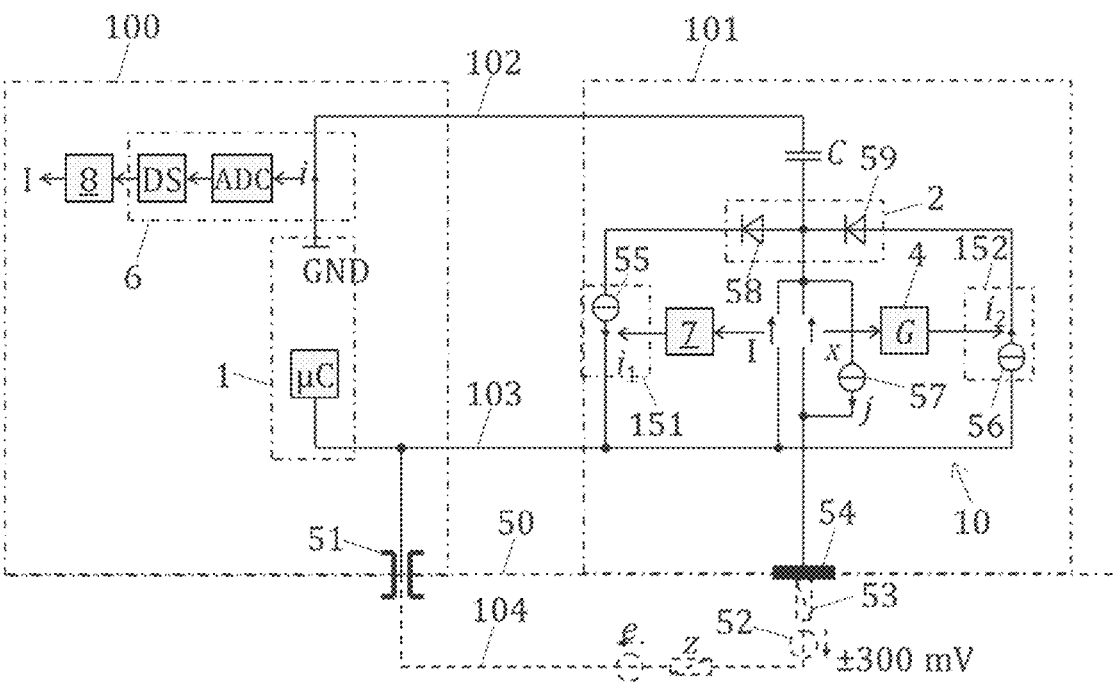
FIG. 4 shows the cooperative sensor device, according to an embodiment.

As shown in FIG. 4, if the first and second electrical connections 102, 103 (instead of body 104) are used for powering of the sensor 101, the 10 mA limit can be increased for instance to 100 mA and use 90 mA for the powering of the sensors 101. A power supply having up to 10% of margin between expected operation and unsafe leakage current is much easier to design than one having only 0.01% (which would correspond to a powering at DC or any other frequencies below 1 kHz).

The first sensor fork sub-circuit 2 can comprise diodes, for example diodes with low forward-voltage drop, like Schottky diodes. Alternatively, the first sensor fork sub-circuit 2 can comprise transistors in order to reduce even further the voltage drop. However, transistors require an active control synchronized with the power voltage v.

The first sensor fork sub-circuit 2 separating the positive and negative currents (i1 and −i2, respectively), allows the control circuit 10 to be configured not only to harvest energy, but also to somewhat influence the current that flows across.

The control circuit 10 can be further configured for controlling the positive or negative current $i_1$, $-i_2$ at a control frequency band since the current to control has always the same direction (either positive or negative, depending on the branch of the first sensor fork sub-circuit 2. Here, the expression "control frequency band" corresponds to a frequencies not overlapping the frequencies of the powering frequency band. The control frequency band can correspond to a range of frequencies used for potential and impedance measurements. For example, the control frequency band comprises an electrode electrochemical voltage frequency band from 0.01 to 0.05 Hz, and/or a bio-potential frequency band from 0.05 to 150 Hz (for ECG), and/or a bio-impedance frequency band from 49.5 to 50.5 kHz (for EIT), and/or a communication frequency band from 0.01 to 2 MHz. Controlling at the control frequency band can reduce the energy consumption of the sensor 101. This can be important for wearables in order to maximize autonomy. This can also be important for the remotely powered sensor 101, due to the safety constraints mentioned above.

In the example of FIG. 1, the sensor 101 comprises a controller 4 with transfer function G and an adder 3, for controlling the first controlled signal x to a desired signal d. In order for the controller 4 to properly work, the first condition is that the first controlled signal x must be controllable (in the sense of control theory). For instance, if the first controlled signal x is independent of any action on the positive current $i_1$, its control to a desired signal d is impossible. The first control signal x may be for instance the voltage between two nodes of the circuit, wherein the "circuit" is to be taken as a whole, i.e., master, bus, sensors and body. For example, in FIG. 1 the first control signal x may be the voltage between the node indicated by the numeral 18 and the node between the two diodes in the first sensor fork sub-circuit 2.

The first control signal x may also be any controllable current or any other controllable quantity. The transfer function G of controller 4 must be designed according to control theory so that stability and performance are reached. The adder 3 combined with the minus sign performs the difference between the desired signal d and the first control signal x. The sensor 101 can comprise an optional configurator 5 to switch between the control sub-circuit 15 and one of the modulating device 7 or the controller 4.

In an embodiment, the sensor 101 comprises a modulating device (MOD) 7 modulating the information signal I transmitted to the receiver 6. The master comprises a demodulating device (DEM) 8 configured for demodulating the modulated information signal I. Modulating the information signal I allows for minimizing the disturbance effect of leakages, as well as to multiplex information when several information signal I from a plurality of sensors 101 are transmitted to the receiver 6.

The modulating device 7 may perform modulation in an analogue fashion, such as amplitude, frequency, or phase modulation, time multiplexing, etc. The modulating device 7 may also perform modulation in digital fashion with the transmission of binary information of samples obtained from and ADC (analogue-to-digital converter) or just a flow of bits like the delta modulation of a delta-sigma ADC.

The receiver 6 can comprise a master fork sub-circuit 16. Since the master fork sub-circuit 6 does not have to harvest energy, it may be simpler than the first sensor fork sub-circuit 2. In fact, the master fork sub-circuit 16 can be virtual. The virtual master fork sub-circuit 16 can results from an operation of down sampling, after that an ADC working at a sampling rate equal to the frequency of the voltage v will have simultaneously acquired the current in both directions.

Figure 2:
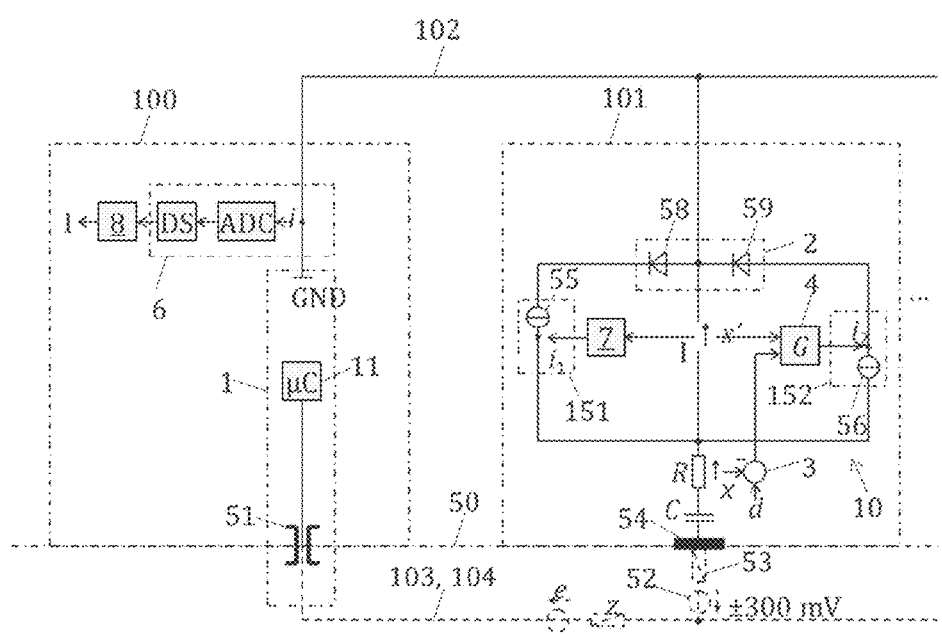
FIG. 2 shows a possible embodiment of the cooperative sensor device of FIG. 1.

FIG. 2 shows a possible embodiment of the cooperative sensor device of FIG. 1. Although one sensor 101 is shown, it should be understood that the cooperative sensor device can comprise one or a plurality of sensors 101. In the example of FIG. 2, the sensors 101 contact a measurable surface 50 of a body 104 via an electrode 54. The measurable surface 50 of the body can be the skin in the case the cooperative sensor device is applied to a human or animal. The electrode 54 can comprises a dry electrode if the admittance and leakage current between the electrode 54 and the electrical connector 102 are small enough (in the measurement frequencies, which are for instance from 0.05 to 150 Hz for ECG and a band of ±500 Hz about 50 kHz for EIT). Gel electrodes accept higher admittance and leakage current, although both must still be kept low for good performances. This contrasts with the current from the power supply (power voltage v) that must be high to transmit enough energy to the sensor 101 and the admittance of the sensor 101 for this current that must also be high, so that the alternating power voltage v of the power supply 1 corresponding to a given power is not too high (e.g., to avoid concerns related to safety and power consumption). The electrode 54 comprises a resistance R and a capacitance C. The difference of voltage x and desired signal d is performed by the adder 3 and inputted in the controller 4.

The first sensor fork sub-circuit 2 is simply made of diodes 58 and 59 (e.g., Schottky diodes). The control circuit 10 comprises a first control sub-circuit 151 including a first controlled current source 55 on the side of one of the diodes 58 and a second control sub-circuit 152 including a second controlled current source 56 on the side of the other diode 59. The voltage on the first and second current sources 55, 56 is always either 0 (when the diode 58, 59 is blocked) or in the same direction as the current (when the diode 58, 59 is conducting). Therefore, the first and second current sources 55, 56 dissipate power that can be harvested if they are appropriately designed.

The power supply 1 can comprise a digital output of a microcontroller μC 11. The master comprises a pass-through circuit 51 that transforms the high impedance of the surface 50 of the body 104 (for example skin) to virtually 0Ω. In order to achieve that, the pass-through circuit 51 can comprise an electrical circuit and two electrodes (symbolized by element indicated under numeral 51). In a configuration not represented, the pass-through circuit 51 can comprise an operational amplifier powered by a voltage source and driving a first electrode (destined to be in contact with the body 104), according to a voltage feedback measured at the electrode. A potential measured at a second electrode (also destined to be in contact with the body 104) is inputted in the operational amplifier (see European patent EP2567657 from the present applicant for more details). The pass-through circuit 51 is preferable than an electrode (like electrode 54) since it has no impedance (such as impedance 53) and prevents disturbance current resulting from ambient electric-field variations (due to mains or motion in Earth electric field) to create a voltage when crossing the surface 50. Such voltage is undesired because it can be seen as 'common mode' since the real voltage of interest is not what one sensor 101 measures, but the difference between the measurements of two sensors 101. However, a too-high common mode may saturate the amplifiers of the sensors 101, 101', which is to be avoided.

The receiver 6 in the master 100 comprises an analog-to-digital converter (ADC) and a down sampling element DS. The information I sent by the sensor 101 to the master 100 via the current $i_1$ is picked up by the ADC which amplifies and samples the current i ($i_1$-$i_2$). Following the ADC, down sampling is performed in the DS element (unnecessary if samples already correspond to $i_1$) so that only the samples corresponding to $i_1$ are further demodulated by the DEM 8 to output the recovered information I.

The first electrical connection 102 comprises an electrically conductive wire and the second electrical connection 103 is the body 104. Therefore, in this configuration, the cooperative sensor device requires only one wire 102. This is particularly advantageous for the integration of the cooperative sensor device in a garment, since the garment can be made of a single conductive yarn, achieving a simplified connection between garment (playing the role of the wire 102) and the master 100 and/or sensors 101. Moreover, as there is only one contact on both sides of the sensors 101, the latter can be easily packaged and made very small (basically a die packaged like a button battery cell, i.e., with a bottom in contact with the body 104 and a top in contact with garment 102).

When performing an impedance measurement, the frequency of the power current can be at 1 MHz, i.e., only 20 times higher than the frequency of a impedance current j (resulting from x/R, x being controlled according to the desired signal d) injected by the sensor 101 to perform the impedance measurement. Small admittance for impedance measurements corresponds to the order of picofarads while high admittance for the power current is in the order of 10 nF, i.e., at least 10000 higher. Such high difference can only be obtained thanks to a feedback loop with a gain ≥10000 for all frequencies in the impedance measurement frequency band.

The transfer function G of the controller 4 has a component corresponding to the voltage x measured on the resistance R and that must therefore have a transfer function with a gain allowing one to reach an open-loop gain ≥10000 in the impedance measurement frequencies while having an open-loop gain ≤1 for frequency equal and greater than 1 MHz. If the desired signal d is zero, no current flows in the impedance measurement band, meaning that the input capacitance C is small, which is what is expected for any good voltage amplifier (here potential e and z·j). If the desired signal d is not zero but a sinewave at 50 kHz, the closed loop will result in a current source (with current equal to d/R and internal impedance corresponding to the input capacitance C described above).

During the impedance measurement, one of the sensors 101 injects a controlled impedance current j and then, measures an impedance voltage resulting from the impedance current j of other sensors 101 on the impedance z to measure an impedance value.

Another sensor 101 drains the same current j (i.e., inject a current −j). At the master 100, the superposition of these two currents j, −j results in no current at all. Two other sensors 101 can measure the resulting potentials with respect to the master 100, but the impedance value will be proportional to the difference of these two potentials. As the sensors 101 injecting the impedance current j are distinct from those measuring the resulting potentials, the impedances of the surface 50 and electrodes 54 do not disturb the measurement.

When performing an ECG measurement, the open-loop gain must also be high in an ECG frequency band in order to measure the voltage e. This can be achieved with the same transfer function G as used in the impedance measurement, and by increasing the gain at low frequency. Note that like for any feedback loops, a proper design should avoid instability.

A second control signal x' is controlled to zero (desired signal d' for x') at very low frequencies by the other component of the transfer function G (typically below 0.05 Hz if ECG is to be measured). Controlling the second control signal x' to zero at very low frequency allows the sensor 101 to reject an electrode electrochemical voltage 52 that can reach ±300 mV, i.e., much higher than the ±10 mV maximum range of the ECG. When rejection is reached, the capacitance C will have been charged by i, i.e., the sum of positive current $i_1$ and negative current −$i_2$ so that its voltage added to the electrochemical voltage 52 is zero (the power supply 1 alternating voltage v and ECG voltage e are both zero at low frequency). Therefore, the second control signal x' corresponds to the information I to be transmitted to the master 100 (in other words, the second control signal x' corresponds to the ECG or EIT measurement signal in their corresponding frequency bands). The modulator 7 insures that the second control signal x' is properly amplified and set up so that it can be transmitted to the master 100 with minimum noise and interference with the environment and with the transmission of information I of other sensors 101'.

Figure 3A:
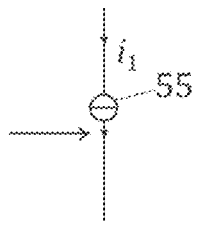
Figure 3B:
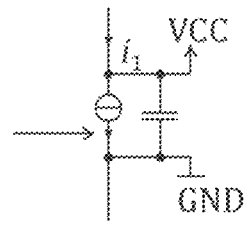
Figure 3C:
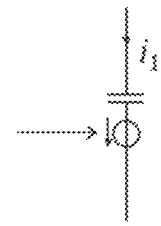
Figure 3D:
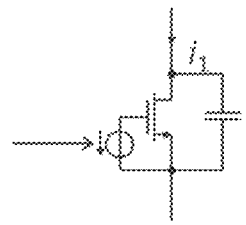

FIGS. 3a to 3g illustrate possible variants of implementation of the control sub-circuit 15 (or first control sub-circuit 151 or second control sub-circuit 152). FIG. 3a shows a variant already illustrated in FIG. 2, where the control sub-circuit 15 comprises a first current source 55 with current $i_1$ proportionally following the analogue control signal. In FIG. 3b, the control sub-circuit 15 further comprises a storage capacitance in parallel of the first current source. This variant is more appropriate for energy harvesting, since the voltage on the capacitance VCC-GND is available also during the time current $i_1$ is equal to 0. However, due to the capacitance in parallel, the current $i_1$ flowing across the first sensor fork sub-circuit 2 (e.g., diode 58) is not anymore equal to the current of the current source since part of $i_1$ flows across the capacitance (which depends on its charge and voltage other parts of the circuit will apply on it). The design of the transfer function G in the controller 4 has to take this effect into account. In the variant shown in FIG. 3c, the control sub-circuit 15 comprises a first voltage source in series with the capacitance (Thevenin equivalent). FIG. 3d illustrates the control sub-circuit 15 comprising an N transistor as current source. In FIG. 3d, the N transistor is a MOS transistor which is therefore controlled with a voltage between its gait and source. This is the reason why a voltage source is used to translate the analogue control signal in the language of electrical diagrams. Of course, bipolar, FET, or any other transistors may also be used.

The variant shown in FIG. 3e allows a direct control of current $i_1$ while harvesting and storing directly usable energy. Here, the control sub-circuit 15 includes the same N transistor as in the variant of FIG. 3d, but the current controlled by the transistor is copied by a current mirror in the parallel branch feeding the capacitance with a current equal to the controlled current. Therefore, $i_1$ will be the sum of the controlled current and the current mirror, but will keep direct proportionality to the control signal. It is more favourable to use a current mirror with amplification, i.e., that lets flow, for example, 10 times more current through the capacitance branch so as to maximize the harvested current. The Zener diode in parallel to the capacitance limits the harvested energy to a level that will never stop the current $i_1$. Additionally, the Zener diode provides a first regulation to the voltage VCC-GND.

Variant of FIG. 3f is similar to the one of FIG. 3e except that the Zener diode has been replaced by a P transistor providing a bypass when the source-drain voltage on the mirror transistor is below a certain value equalled to −Th, where Th is the threshold of this additional P transistor working in depletion mode (i.e., transistor blocked when its voltage gate-drain is high). The variant of FIG. 3f has the advantage that the current $i_1$ is still proportionally following the voltage source driving the transistor when the voltage on the control sub-circuit 15 is smaller than the voltage on the capacitance, for instance when in FIG. 2 there is a significant voltage drop across the body impedance 53 (skin impedance) due to the injection of current (signal d different from zero). During the time the current is bypassed by the depletion-mode P transistor, no energy is harvested, but it is assumed that the storage capacitance is high enough to bridge the bad-harvest periods. The diode prevents the harvested energy stored in the capacitance to flow back via the depletion-mode P transistor when $i_1$ is 0 (idle period).

The variant shown in FIG. 3g is based on a switch actuated by a modulator translating the analogue control signal to a binary signal suitable for the switch, e.g., a PWM (pulse wave modulation). More advanced harvesting schemes are possible. Of course, the same architecture shown in FIGS. 3a-3g for the positive current $i_1$ applies for the negative current $-i_2$, mutatis mutandis.

Using only one wire, such as in the embodiment of FIG. 2, wherein the first electrical connection 102 comprises an electrically conductive wire and the second electrical connection 103 is the body 104, may be disadvantageous for some applications. For instance, it limits the number of sensors 101 since the powering current flows across the body. The number of sensors 101 depends on the power consumption of each sensor 101. Moreover, the parasitic capacitance at the amplifier input (at x) and of the current-source cannot be reduced below a certain value due to the presence of the power signal frequency close to the impedance measurement frequency band.

A second electrically conductive wire 103 different from the body 104 can significantly remedy to this drawback (but to the price of an additional wire).

FIG. 4 shows the cooperative sensor device, where both the first and second electrical connections 102, 103 comprise an electrically conductive wire, according to an embodiment. In contrast to the configuration of FIG. 2, the cooperative sensor device of FIG. 4 use another control loop (controller G) to increase the open-loop impedance. The open-loop impedance is not drawn in FIG. 4 (i.e., considered as infinite), but is in reality the amplifier input impedance and the impedance of a third current source 57, both taken in parallel. The controller 4 controls the first control signal x to zero when the loop is closed. This means that if the open-loop gain is g, the closed-loop impedance at x will correspond to the open-loop impedance multiplied by g+1. It is thus easy to get good amplifier and current source (i.e., with high impedance). The open-loop gain depends on G, but also on the transconductance of the controlled current source $i_2$ and the capacitance C. The information I to be transmitted is the voltage measured between the wire 103 and the node in the middle of the first sensor fork sub-circuit 2. This node has the same potential as that of the electrode 54 (thanks to x controlled to zero as described above) and therefore, either this node or the electrode 54 can be used to measure the voltage to be transmitted to the master 100.

Since x is controlled to zero by the transfer function G of the controller 4, the voltage on capacitance Cis equal to the information I, except for the component at the power signal frequency. In particular, the voltage on capacitance C does not directly depend on the current j of current source 57. In other words, the whole current j injected in the body by the current source 57 returns via the wire 103 (no part of it returns via wire 102). If one considers that in reality wires 102 and 103 have impedances (which are not drawn in the simplified model of FIG. 4), current j will induce a disturbance on the impedance of wire 103 that will be part of the information I as taken in FIG. 4 but not if the information I is taken from the voltage on capacitance C. However, the voltage taken on capacitance C will not totally be undisturbed by the impedance of wire 102, because this impedance makes a voltage divider with C. The current flowing across the voltage divider has however also to come from wire 103, and the disturbance of wire 102 due to this effect will be positively added to the disturbance on wire 103 due to current j. Less disturbance is therefore expected if the information I is taken from the voltage on C. Besides, the smaller the capacitance C or the impedance of wire 102 is, the smaller will be the disturbance.

Figure 5:
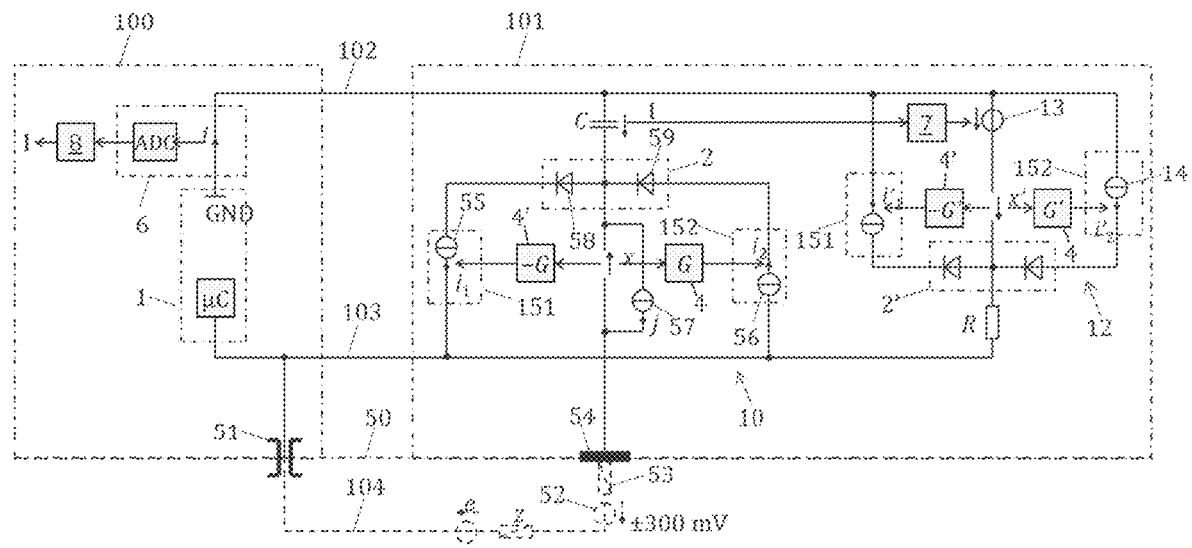
FIG. 5 shows the cooperative sensor device comprising a second sub-circuit, according to an embodiment.

The potentials on capacitance C is beyond the range of potentials provided by the harvesters of the current sources 55 and 56. This may be a difficulty, depending on the electronic technology available. In order to address this issue, the embodiment of FIG. 5 comprises a second control circuit 12 built about a second sensor fork sub-circuit 2' in an arrangement head to tail with the control circuit 10 built about the first sensor sub-circuit 2. The two branches of the control circuit 10 are used for the controlling of voltage x to 0, thanks to a second controller 4' with opposite transfer function −G, while the second control circuit 12 takes over the function of sending the information I. The variant of FIG. 5 illustrates the high number of variations offered by the invention where the second control circuit 12 uses an amplitude modulation performed by the MOD 7. The modulation carrier used for information I is a sinewave at lower frequency than the power signal frequency but in a band different than the one of the ECG and EIT. The voltage source 13 controlled by MOD 7 sets the voltage on the resistance R, since the second control signal x' is equal to zero thanks to G' and −G', (the voltage of the power supply 1 is zero at the modulation carrier frequency). The voltage source 13 in series with the second control signal x' can perform an addition function, equivalent to the adder 3. Therefore, the current flowing across R is directly proportional to the signal modulated by MOD 7 and can be recovered by the receiver 6 before being demodulated by DEM 8. Several cooperative sensors 101 can use different modulation carriers (i.e., frequency multiplexing). As a variant, R can be replaced by a capacitance. In this case, the information will be physically transferred by a charge signal rather than a current signal and the current i must be integrated in the receiver 6 (for instance by taking the voltage of a capacitance crossed by a current proportional to i, or digitally after the ADC).

Figure 6:
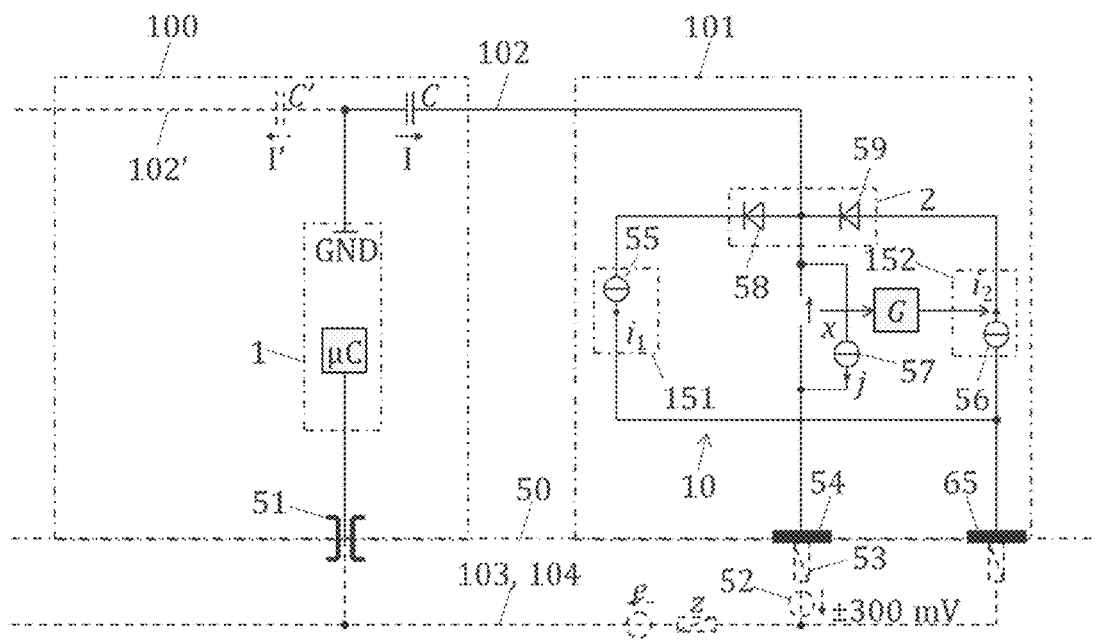
FIG. 6 shows the cooperative sensor device, according to an embodiment.

When there is only one sensor 101 on a given 2-wire bus, i.e., connected to the first and second wire 102, 103 (there may be several independent 2-wire bus radiating from the master), the capacitance C can be comprised in the master 100 itself, as shown in the embodiment of FIG. 6. In this case, the master 100 directly measures the voltage I and there is no need to use a modulation to transmit the information I.

Figure 7:
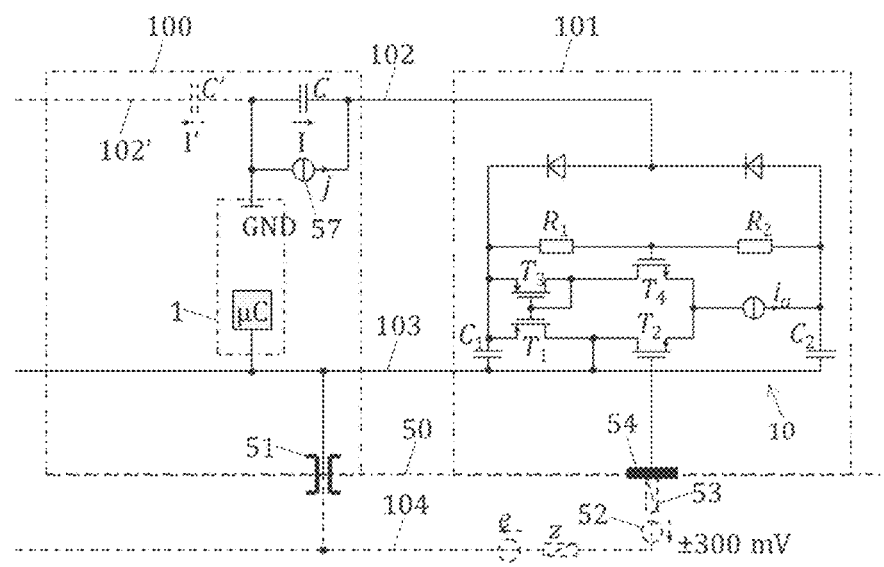
FIG. 7 shows an implementation example of the embodiment of FIG. 6.

Alternatively, the master may also comprise the third current source 57, which will be in this case in parallel to the capacitance C (see FIG. 7). The information I coming from a second 2-wire bus, on which only one other sensor 101 is connected, is shown by the dashed line. Note that the configuration of FIG. 6 allows for adding a second electrode 65 such that the second electrical wire 103 is the body 104.

FIG. 7 shows an implementation example of the embodiment of FIG. 6, for its variant with one electrode 54, where the first and second wire 102, 103 comprise a wire, and where the third current source 57 is comprised in the master 100. The first sub-circuit $A_1$ is implemented with a transistor T1 (first current source 55) and a capacitance C1. Likewise, the second sub-circuit $A_2$ is implemented with a transistor T2 (current source 56) and a capacitance C2. The voltage x is taken, thanks to the differential pair (transistor T1 to T4 and constant current source $i_a$), between the potential of electrode 54 and the potential set by the resistance divider R1, R2. The latter is preferred to the potential of the middle node of the first sensor fork sub-circuit 2, because its power signal frequency component is largely attenuated, while its component within the ECG and EIT frequency bands is substantially unaltered. Note that the differential pair is standard circuit widely used in operational amplifiers (OPA) where they constitute their input stage. Needless to say that any advanced implementation of differential pair used for operational amplifiers can be used also in the invention context. Instead of using only the input stage of the operational amplifier, a full operational amplifier may also be used. However, as the middle stage of an operational amplifier is an integration and the output stage a controlled voltage source, a compensation circuit must be added so that the arrangement is stable (according to control theory). Operational transconductance amplifier (OTA) are more appropriate as alternative to bare differential pairs.

Figure 8:
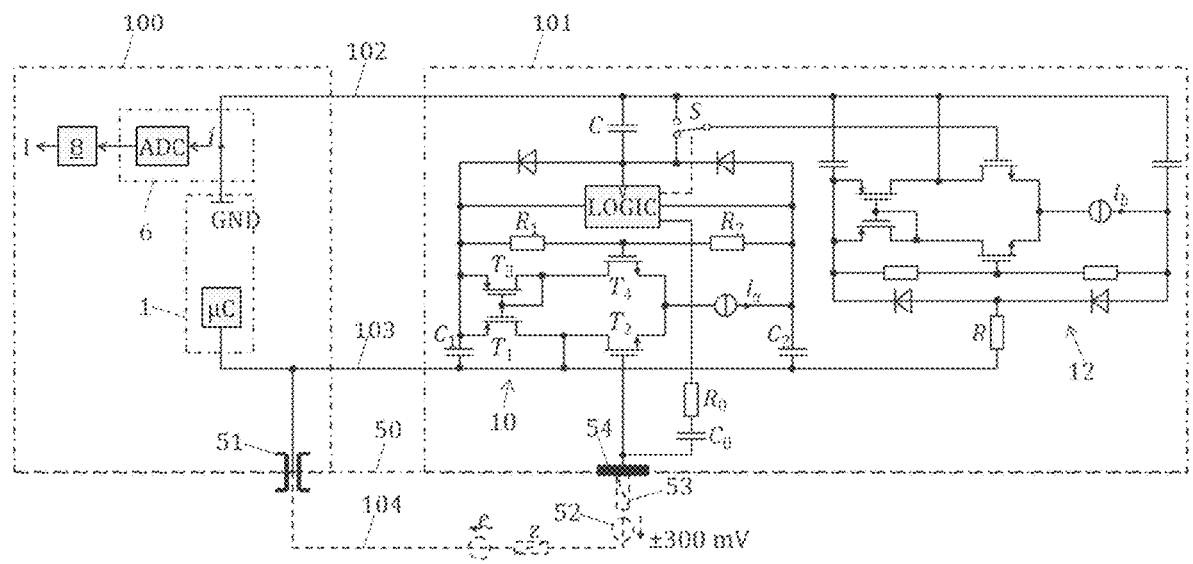
FIG. 8 shows an implementation example of the cooperative sensor device, according to the embodiment of FIG. 5.

FIG. 8 shows an implementation example of the cooperative sensor device according to the embodiment of FIG. 5. The use of the differential pair is identical to that of FIG. 7. The control circuit 10 comprises a block LOGIC that is powered from capacitance $C_1$ and $C_2$ and mainly contains logic circuits but may also include other components like energy-storage capacitances or voltage regulators. Its input is the clock taken from the middle node of the first sensor fork sub-circuit 2. The LOGIC divides this clock by 20 (if EIT frequency is 50 kHz and power supply 1 is at 1 MHz) and the generated signal is used together with the resistance $R_0$ to implement the third current source 57 with a Thevenin transformation. The impedance of the third current source 57 is therefore $R_0$, the value of which being determined by the injected current j and the LOGIC voltage. This resistance is in general too small to make an ideal current source. This is however not a big issue, since the gain of the control loop including G is assumed high enough to significantly increase the impedance of the current source as seen from e. The capacitance $C_0$ contributes to increase the impedance at low frequencies (where current is 0), but its purpose is also to make sure that no DC current flows across the body (for safety reason as well as not to create a voltage drop on the skin impedance 53 that would disturb the measurement of e). The voltage on the capacitance C (which is the information to transmit to the master 100) is modulated by the switch S actuated by the LOGIC. The modulation is equivalent to the multiplication of the signal by 1 or 0, depending on the signal actuating the switch. This signal may be a square wave of a given frequency (frequency multiplexing) or it may be 1 only for a short time defining a time slot (time multiplexing). The remaining of the circuit implemented functions have been explained above.

Figure 9:
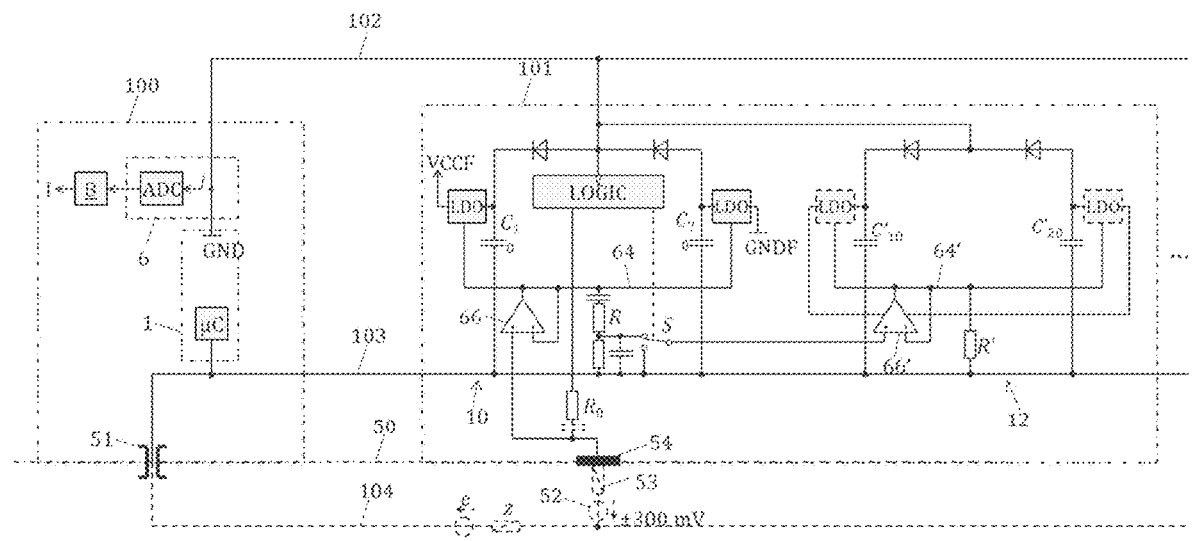
FIG. 9 shows another implementation example of the cooperative sensor device, according to the embodiment.

FIG. 9 shows another implementation example of the cooperative sensor device according to the embodiment. The circuit of FIG. 9 has basically the same functionalities as those of the circuit of FIG. 8, but is easier to implement with discrete components. In particular, a control current for the positive and negative branches (positive current $i_1$ and negative current $-i_2$) is set by the output stage of the operational amplifier 66. In order to ensure stability, the output resistance of the operational amplifier 66 should be at most equal to the resistance R and the capacitances large enough so that the corner frequency of the RC circuit is about a decade lower than the GBP (gain-bandwidth product) of the operational amplifier 66. As far as the behaviour of the control loop is concerned, the wire 103 is equivalent to electrode 54 and, therefore, the operational amplifier 66 can be considered as connected over the RC circuit. Note that in contrast to the circuit of FIG. 4, there is no capacitance C connected to the wire 103. This is necessary, since the LDOs (low-dropout voltage regulators) define VCCF and GNDF as DC potentials relative to line 64 (and no longer directly related to the middle point of the first fork sub-circuit 2). However, the latter feature is beneficial because both terminals of the RC circuit as well as the internal node of this circuit are easily accessible by the electronics (within the power-supply range GNDF-VCCF). The latter feature is also beneficial because it allows the current injected in (or drained from) the body via $R_0$ to completely return via the wire 102. Wire 103 is therefore undisturbed by this current and used for the measurement of potential via amplifier 61. Any variation of resistances of lines 102 and 103, e.g., due to variations of tension on a conductive fabric, will not disturb the measurement of z. The RC circuit, in addition to behave as resistance Rat GBP frequency as mentioned above, provides at its internal node a potential (with respect to wire 103) equal to the measured biopotential e and voltage on impedance z after band-pass filtering (in the example of FIG. 9). Switch S is used for the same purpose as in FIG. 8, i.e., to perform the modulation to transmit the information I to the master 100, which is done by the operational amplifier 66' that transforms the voltage coming from the switch S to the current i measured in the master 100 tanks to the resistance R'. The operational amplifier 66' is separately powered by its own LDOs and harvester, but its principle of operation is identical to what has been described for the operational amplifier 66. The operational amplifier 66' may also be directly connected to the storage capacitances $C'_{10}$ and $C'_{20}$ without LDOs.

Figure 10:
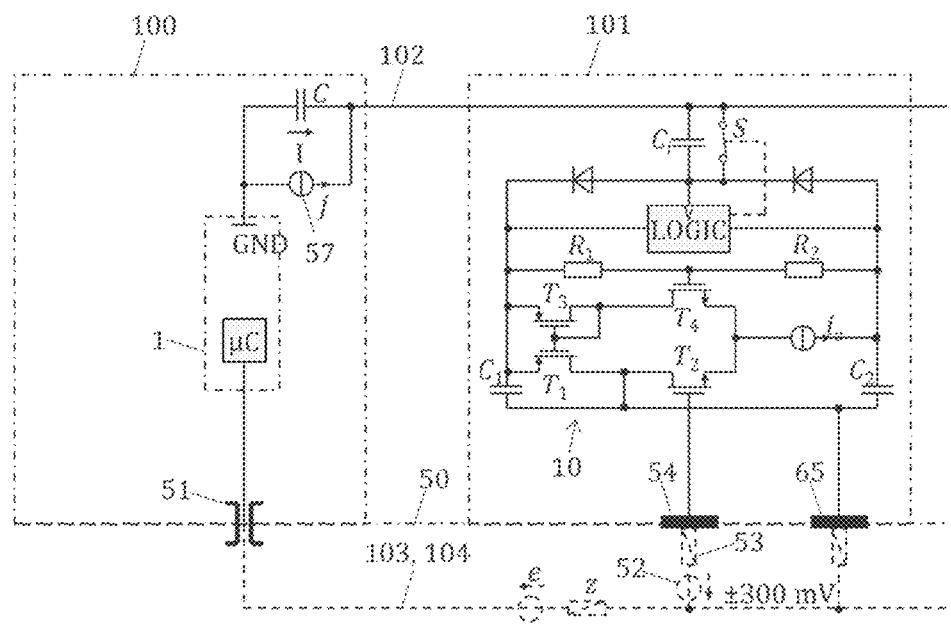
FIG. 10 shows yet another variant combining the simplicity of the variant of FIG. 7.

FIG. 10 shows yet another variant combining the simplicity of the variant of FIG. 7 and the possibility to multiplex several sensors 101 on the same 2-wire bus as in the configuration of FIG. 8. Only one of the sensors 101 has, during a time period, its switch S closed (as control by the LOGIC). The sensor 101 having its switch closed stores its information I on the capacitance C of the master 100, as shown in FIG. 7. During the same time period, the other sensors 101 have their switch S open and they have a voltage on $C_i$ being equal to the difference between their information I and the information I of the sensor 101 with the closed switch S. Then, another sensor 101 has its switch S closed and transmits its information I, while the other sensors 101 have their switch S open.

Figure 11:
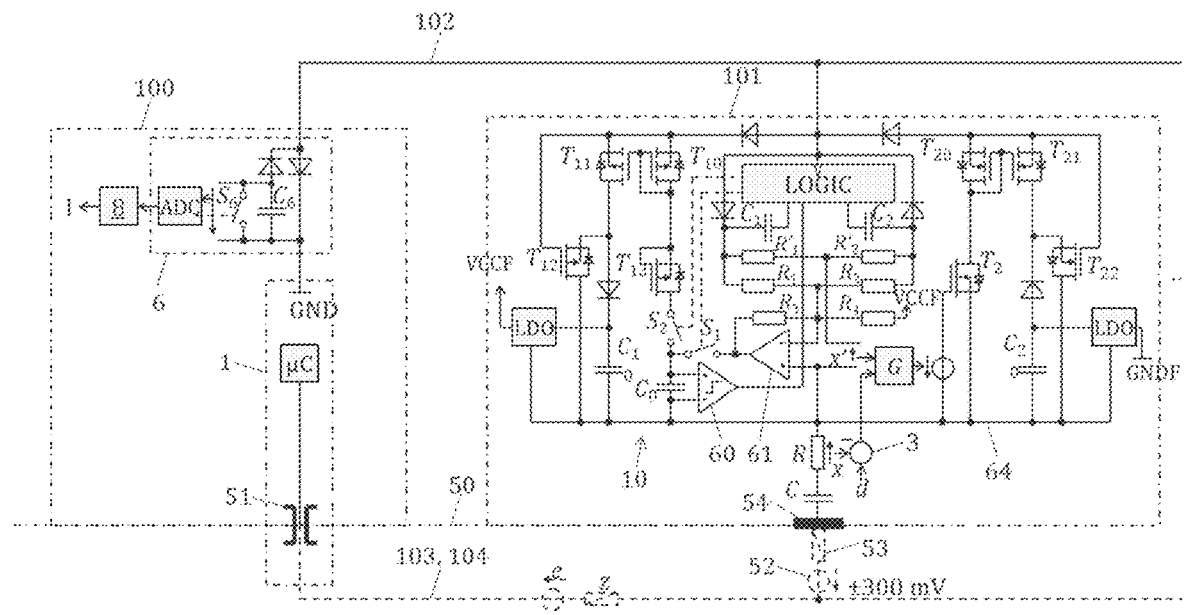
FIG. 11 shows yet another variant of the cooperative sensor device, where only one electrical connection comprises a wire.

FIG. 11 shows yet another variant of the cooperative sensor device, where only the first electrical connection 102 comprises a wire (such as in the embodiment of FIG. 2). Here, the first sub-circuit $A_1$ and the second sub-circuit $A_2$ are implemented according to the variant of FIG. 3f, i.e., the second sub-circuit $A_2$ comprises transistors $T_{20}$, $T_{21}$, $T_{22}$ and capacitance $C_{20}$. LDOs are used to provide regulated potentials VCCF and GNDF, for instance 1 V above and 1 V below the middle-potential line 64, respectively. All active components (LOGIC, comparator 60, operational amplifier 61, controller G, etc.) are powered with VCCF and GNDF. The transistor $T_2$ sets the current according to the controller G. The LOGIC is driven by a clock in the same way as in the previous examples (FIGS. 8 to 10). In contrast to the configuration of FIG. 2, where the second control signal x' is referred to the middle node of the first sensor fork sub-circuit 2, a middle point with a lower component at 1 MHz is created in a similar way as the previous examples (FIGS. 7 to 8 and 10), i.e., with diodes, resistances $R'_1$ and $R'_2$, and capacitances $C_1$ and $C_2$. These components are different from those used for the other functions of the circuit because the voltages on capacitance $C_{10}$ and $C_{20}$ is actively controlled and are different from those on capacitances $C_1$ and $C_2$. The capacitance $C_1$ and $C_2$ have one of their terminal connected to the LOGIC with low level for $C_1$ and high level for $C_2$. The voltage x' is amplified with the operational amplifier 61 configured with resistances $R_1//R_2$ and $R_3$. Resistances $R'_1$ and $R'_2$ are identical (or at least with the same ratio) to resistances $R_1$ and $R_2$, but cannot be the same physical components, since $R_1//R_2$ is loaded by resistance $R_3$ and $R_4$. Resistance $R_4$ adds a constant negative offset to the second control signal x' so that the output potential of the operational amplifier 61 is never above the middle-potential line 64. This way, the capacitance $C_0$ is always negatively charged when $S_1$ is closed, which happens during the period of current $i_2>0$. During the other periods, $S_2$ is closed as long as the voltage on $C_0$ is negative, as measured by the comparator 60. This means that during the period of current $i_1>0$ (and of transistor $T_{11}$ being blocked), the capacitance $C_0$ is discharged and its variation of charge is transferred to capacitance $C_6$ in the master. The capacitance $C_6$ had been reset with the switch $S_6$, closed during the same period as $S_1$ is closed. Therefore, the ADC measures a voltage proportional to the second controlled signal x'. Transistor $T_{13}$ is configured so that it behaves like a current limitation to progressively and regularly discharge the capacitance $C_0$ to let the comparator 60 accurately switch off the discharge process.

When several sensors 101 are used, it is advantageous to use a specific time slot for the transmission of second controlled signal x' (information I) of any given sensor 101. Therefore, when one sensor 101 is transmitting its charge (modulated information I) to the master 100, the other sensors 101 keep their switch $S_2$ open, so that no current flows except for the transmitting sensor 101. This results in a better control of the charge transfer from $C_0$ to $C_6$. The LOGIC level applied on capacitances $C_1$ and $C_2$ are reversed during the transmission time, so that the diodes block to avoid any communication disturbance due to a current flowing across them.

Figure 12:
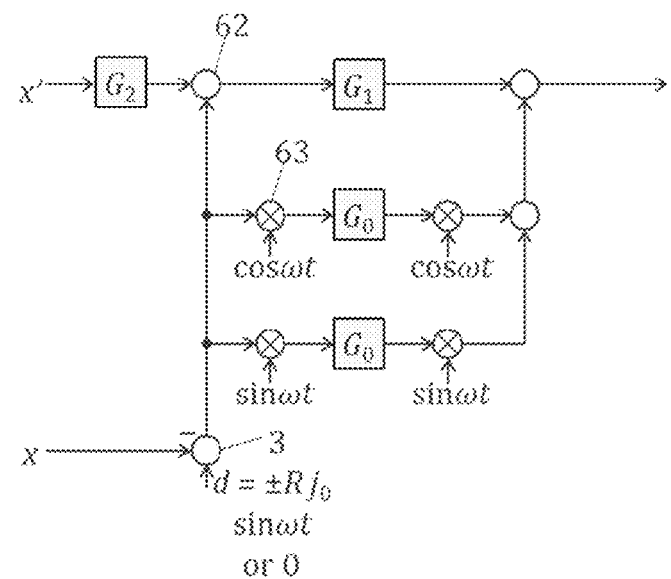
FIG. 12 shows a detailed view of a controller of the cooperative sensor device, according to an embodiment.

FIG. 12 shows a detailed view of the controller 4, according to an embodiment. If the resistance R is chosen equal to 20Ω, a gain of ~16000 is required for this resistance to be ~320 kΩ, which is the minimum impedance expected for an EIT amplifier or current source (it corresponds to 10 pF at 50 kHz). A way to achieve the requirement to have a gain for G at least 16000 times higher within the EIT band (±500 Hz about 50 kHz) than at the powering frequency (1 MHz) is to use a resonant filter. An implementation of a resonant filter may be with the multipliers 63 mixing together the difference x−d with a sinewave and cosine wave at 50 kHz ($\omega=2\pi\cdot 50$ kHz) followed by a transfer function $G_0$ before a second multiplication with the same sinewave and cosine wave finally summed together. The unity gain of the open-loop transfer function must not exceed about 100 kHz (2·50 kHz). Therefore, the integrator of $G_0$ must have a gain compliant with this constraint. As an integrator alone can provide only a gain of 200 at 500 Hz (100 kHz/500 Hz), the low-frequency gain must be increased with PI controllers. The corner frequency of the first PI controller must not be much higher than 10 kHz in order not to destroy too much the phase margin of $G_0$. This provides an additional gain of 20 at 500 Hz. An additional PI controller with corner frequency of 5 kHz provides a further gain of 10. In total, the gain of $G_0$ at 500 Hz reaches 40 000 which is better than the objective. The desired signal d is 0 when no EIT current j is to be injected and a 50 kHz sinewave of amplitude of $\pm R\, j_0$ when the EIT current of 100 μA has to be injected (positive sign) or drained (negative sign). For the ECG frequency band, another controller $G_1$ takes over at low frequencies. In order to reject the electrode electrochemical potential 52, frequencies below 0.05 Hz are discarded thanks to the control of the second control signal x' to 0 with the controller $G_2$ and the adder 62.

Figure 13:
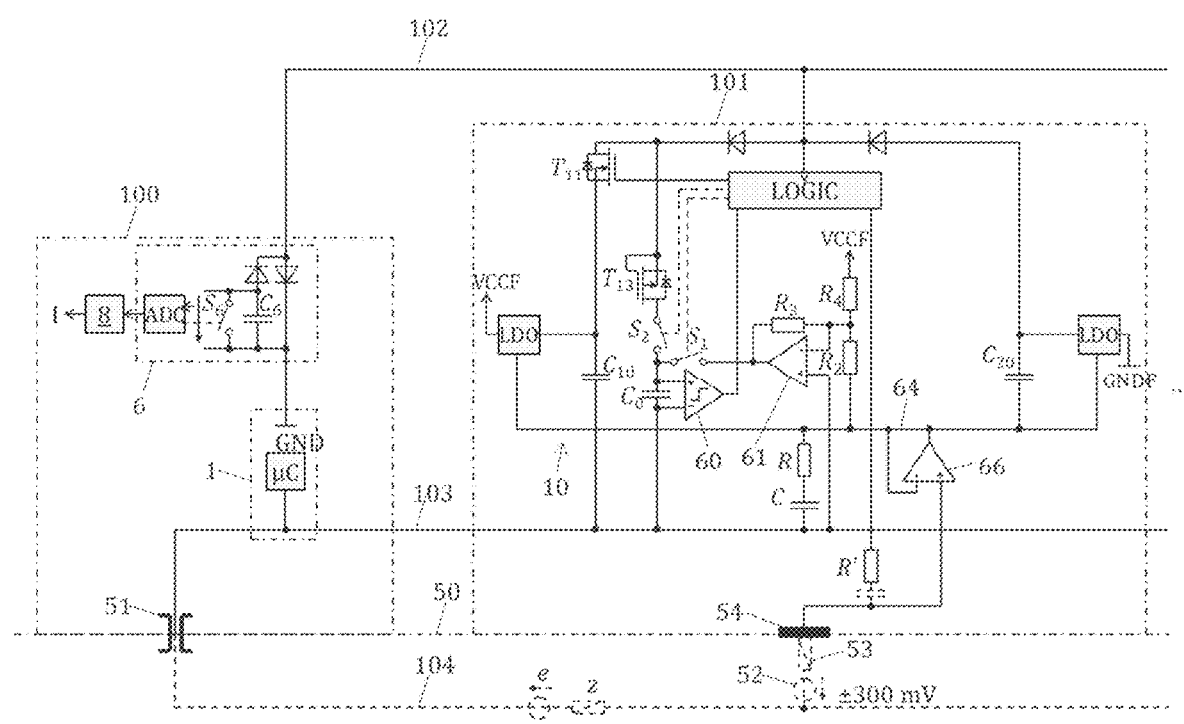
FIG. 13 shows the cooperative sensor device, according to another embodiment.

FIG. 13 shows the cooperative sensor device according to an embodiment similar to the one of FIG. 11 but adapted to a 2-wire configuration and with inspiration of the variant of FIG. 9. Every other 1 MHz cycle, $T_{11}$ is closed to recharge the capacitance $C_{10}$. When $T_{11}$ is open and the current positive, the transmission of information is performed.

REFERENCE NUMERAL USED IN THE FIGURES 1 power supply
2 first sensor fork sub-circuit
2' second sensor fork sub-circuit
3 adder
4 controller (transfer function G)
4' second controller (transfer function −G)
5 configurator
6 receiver 7 modulator
8 demodulator
10 control circuit
11 microcontroller
12 second control circuit
13 voltage source
15 control sub-circuit
16 master fork sub-circuit
18 node
50 measurable surface of body, skin
51 pass-through (circuit)
52 electrode (electrochemical) voltage
53 (electrode and) skin impedance
54 electrode
55 first current source
56 second current source
57 third current source
58, 59 diode
60 comparator
61 operational amplifier
62 logical symbol for the addition of two signals
63 logical symbol for the multiplication of two signals
64 middle-potential line
65 (second) electrode (of bi-electrode sensors)
66 operational amplifier
100 master
101 sensor
102 first electrical connection (first wire)
103 second electrical connection (second wire)
104 body
151 first control sub-circuit
152 second s control ub-circuit
B, C (other) sub-circuits
C capacitance
d desired signal
DS down sampling
e (bio) potential
G (transfer function of) controller
GND ground
GNDF (local) ground (floating with respect to GND)
I information signal
i current
$i_a$, $i_b$ current (of current source)
$i_1$ (positive) current
$-i_2$ (negative) current
j current (injected for the measurement of impedance z)
LOGIC logic circuit
N number of cooperative sensors
R resistance
S switch
T transistor
x first control signal
x' second control signal
v power voltage (source of power supply)
VCC power-supply voltage
VCCF (local) power-supply voltage (floating with respect to VCC)
y (thevenin-equivalent internal) impedance (of power supply)
z (bio) impedance
μC microcontroller
ω angular frequency

The invention claimed is:

1. A sensor for potential and/or impedance measurements on a body, comprising a master and at least one remotely powered sensor connected to the master;

the master comprising a receiver and a power supply configured to supply an alternating power voltage to said at least one remotely powered sensor;

each of said at least one remotely powered sensor comprising a control circuit including a first sensor fork sub-circuit configured to supply a positive current to a first circuit branch and a negative current to a second circuit branch;

each of said at least one remotely powered sensor further comprising an electrode and being configured to perform the potential and/or impedance measurements when the electrode is in contact with the body;

the control circuit further comprising a control sub-circuit configured for controlling the positive and/or negative current in order to transmit an information signal to the receiver, and/or to control a first controlled signal to a first desired signal;

wherein the control circuit is further configured to control the positive and/or negative current at a control frequency band corresponding to a range of frequencies used for the potential and/or impedance measurements;

each of said at least one remotely powered sensor further comprising a first electrical connection and a second electrical connection connecting each of said at least one remotely powered sensor to the master, each of said at least one remotely powered sensor being powered via the first and second electrical connections;

wherein the power supply is configured to supply the alternating power voltage at a powering frequency band;

wherein the control circuit is configured for harvesting energy from the alternating power voltage to power each of said at least one remotely powered sensor; and wherein the first sensor fork sub-circuit comprises two diodes or transistors, the first electrical connection connecting the first sensor fork sub-circuit to the master at a node between the two diodes or transistors.

2. The sensor according to claim 1, wherein the control sub-circuit is connected to at least one of the two diodes or transistors.

3. The sensor according to claim 1, wherein the two diodes or transistors are connected between the first electrical connection and the second electrical connection in parallel.

4. A sensor for potential and/or impedance measurements on a body, comprising a master and at least one remotely powered sensor connected to the master;

the master comprising a receiver and a power supply configured to supply an alternating power voltage to said at least one remotely powered sensor;

each of said at least one remotely powered sensor comprising a control circuit including a first sensor fork sub-circuit configured to supply a positive current to a first circuit branch and a negative current to a second circuit branch;

each of said at least one remotely powered sensor further comprising an electrode and being configured to perform the potential and/or impedance measurements when the electrode is in contact with the body;

the control circuit further comprising a control sub-circuit configured for controlling the positive and/or negative current in order to transmit an information signal to the receiver, and/or to control a first controlled signal to a first desired signal;

wherein the control circuit is further configured to control the positive and/or negative current at a control frequency band corresponding to a range of frequencies used for the potential and/or impedance measurements;

each of said at least one remotely powered sensor further comprising a first electrical connection and a second electrical connection connecting each of said at least one remotely powered sensor to the master, each of said at least one remotely powered sensor being powered via the first and second electrical connections;

wherein the power supply is configured to supply the alternating power voltage at a powering frequency band;

wherein the control circuit is configured for harvesting energy from the alternating power voltage to power each of said at least one remotely powered sensor; and wherein the first electrical connection connects the power supply to the first sensor fork sub-circuit and the second electrical connection connects the receiver to the control circuit.

* * * * *